United States Patent [19]
Ringeisen et al.

[11] Patent Number: 5,935,594
[45] Date of Patent: *Aug. 10, 1999

[54] PROCESS AND DEVICE FOR TREATING AND HEALING A TISSUE DEFICIENCY

[75] Inventors: Timothy Ringeisen; John H. Brekke, both of Duluth, Minn.

[73] Assignee: THM Biomedical, Inc., Duluth, Minn.

[ * ] Notice: This patent is subject to a terminal disclaimer.

[21] Appl. No.: 09/055,826

[22] Filed: Apr. 6, 1998

Related U.S. Application Data

[62] Division of application No. 08/637,651, filed as application No. PCT/US94/12424, Oct. 28, 1994, Pat. No. 5,736,160, and a continuation of application No. 08/144,714, Oct. 28, 1993, abandoned.

[51] Int. Cl.$^6$ .................................................. A61K 9/16
[52] U.S. Cl. .................. 424/426; 424/422; 424/423; 424/428; 424/434; 424/437; 424/444; 424/487; 523/122; 524/5; 521/182; 525/415; 604/890.1
[58] Field of Search .................................. 424/422, 423, 424/426–428, 434, 437, 438, 444, 457; 523/105–112, 115, 122; 524/5, 599; 521/182, 185; 525/415, 450; 604/890.1

[56] References Cited

U.S. PATENT DOCUMENTS

| | | |
|---|---|---|
| 2,465,357 | 3/1949 | Correll .............................. 128/296 X |
| 2,610,625 | 9/1952 | Sifferd et al. ......................... 128/296 |
| 2,621,145 | 12/1952 | Sano . |
| 2,703,316 | 3/1955 | Schneider . |
| 2,758,987 | 8/1956 | Salzberg . |
| 3,463,158 | 8/1969 | Schmitt et al. . |
| 3,491,760 | 1/1970 | Braun et al. ......................... 128/335.5 |
| 3,636,956 | 1/1972 | Schneider .......................... 128/335.5 |
| 3,688,317 | 9/1972 | Kurtz ................................... 128/334 R |
| 3,739,773 | 6/1973 | Schmitt et al. ......................... 606/62 |
| 3,902,497 | 9/1975 | Casey . |
| 3,937,223 | 2/1976 | Roth ..................................... 128/296 |
| 4,164,560 | 8/1979 | Folkman et al. . |
| 4,181,983 | 1/1980 | Kulkarni . |
| 4,186,448 | 2/1980 | Brekke ................................... 613/14 |
| 4,279,249 | 7/1981 | Vert et al. . |
| 4,357,312 | 11/1982 | Hsieh et al. . |
| 4,419,340 | 12/1983 | Yolles . |
| 4,442,655 | 4/1984 | Stroetmann ........................... 623/16 |
| 4,505,266 | 3/1985 | Yannas et al. ......................... 623/15 |
| 4,553,272 | 11/1985 | Mears .................................... 623/16 |
| 4,563,350 | 1/1986 | Nathan et al. ......................... 623/16 |
| 4,563,489 | 1/1986 | Urist ...................................... 623/16 |
| 4,578,384 | 3/1986 | Hollinger ................................. 519/8 |
| 4,596,574 | 6/1986 | Urist ...................................... 623/16 |
| 4,608,199 | 8/1986 | Caplan et al. . |
| 4,609,551 | 9/1986 | Caplan et al. . |
| 4,620,327 | 11/1986 | Caplan et al. . |
| 4,636,526 | 1/1987 | Dorman et al. . |
| 4,642,120 | 2/1987 | Nevo et al. . |
| 4,713,076 | 12/1987 | Draenert ................................ 623/16 |

(List continued on next page.)

FOREIGN PATENT DOCUMENTS

| | | |
|---|---|---|
| 1274179 | 9/1990 | Canada . |
| 0277678 | 10/1988 | European Pat. Off. . |
| 0369034 | 5/1990 | European Pat. Off. . |
| 0505634 | 9/1992 | European Pat. Off. . |
| 0567391 | 4/1993 | European Pat. Off. . |
| 0567391 | 10/1993 | European Pat. Off. . |
| 3841397 | 12/1988 | Germany . |
| 63-238867 | 10/1988 | Japan . |
| 323864 | 1/1991 | Japan . |
| 2164024 | 5/1985 | United Kingdom . |
| 2175506 | 12/1986 | United Kingdom . |
| WO 8600533 | 1/1986 | WIPO . |
| WO 8803785 | 6/1988 | WIPO . |
| WO 9009783 | 9/1990 | WIPO . |
| WO 9015586 | 12/1990 | WIPO . |
| WO 9315694 | 8/1993 | WIPO . |
| WO 9320859 | 10/1993 | WIPO . |
| WO 9409722 | 5/1994 | WIPO . |

OTHER PUBLICATIONS

Resorbable Ceramic Implants, G.A. Graves et al., Bioceramics—Engineering in Medicine (Part 1), J. Biomedical Materials Symposium, No. 2, pp. 91–115 (1972).

Application of Porous Ceramics for the Attachment of Load Bearing Internal Orthopedic Applications, J.J. Klawitter et al., Bioceramics—Engineering in Medicine (Part 1), J. Biomedical Materials Symposium, No. 2, pp. 161–129 (1972).

Compatibility of Porous Ceramics with Soft Tissue; Application to Tracheal Prosthesis, S.F. Hulbert et al., Bioceramics—Engineering in Medicine (Part 1), J. Biomedical Materials Symposium, vol. 2, (Part 1), pp. 269–279 (1972).

Bioceramics—Engineering in Medicine (Part 2), J. Biomedical Materials Symposium, R. Topazian et al., No. 2 (Part 2), pp. 311–332 (1972).

Development of Ceramic and Ceramic Composite Devices for Maxillofacial Applications, T.D. Driskell et al., Bioceramics—Engineering in Medicine (Part 2), J. Biomedical Materials Symposium, No. 2 (Part 2), pp. 345–361 (1972).

Effect of the Structure of Poly(Glycol Monomethacrylate) Gel on the Calcification of Implants, L. Sprinel et al., Calc. Tiss., Res. 13, pp. 63–72 (1973).

(List continued on next page.)

*Primary Examiner*—Neil S. Levy
*Attorney, Agent, or Firm*—Alan Kamrath; Peterson, Wicks, Nemer & Kamrath, PA

[57] ABSTRACT

An improved method or process and device for treating and healing a bone void is disclosed, and in particular a method employing a surfactant for efficiently incorporating a biologically active agent into the interstices (voids or pares) of a porous hydrophobic biodegradable material wherein the biologically active agent is deposited on the internal surfaces defining the voids or pores of the biodegradable material. The biodegradable body or device, now containing surfactant and a biologically active agent in the body itself as well as on the external surfaces and the internal surfaces defining the voids or pores, is than applied into the bone void or cavity.

26 Claims, No Drawings

U.S. PATENT DOCUMENTS

| | | |
|---|---|---|
| 4,749,585 | 6/1988 | Greco et al. ................................ 427/2 |
| 4,752,294 | 6/1988 | Lundgren . |
| 4,846,835 | 7/1989 | Grande ...................................... 623/11 |
| 4,938,763 | 7/1990 | Dunn et al. . |
| 4,962,091 | 10/1990 | Eppstein et al. ............................ 514/2 |
| 4,964,868 | 10/1990 | Bloebaum ................................. 623/20 |
| 5,041,138 | 8/1991 | Vacanti et al. . |
| 5,061,281 | 10/1991 | Mares et al. .............................. 623/11 |
| 5,077,049 | 12/1991 | Dunn et al. . |
| 5,078,744 | 1/1992 | Chvapil .................................... 623/16 |
| 5,133,755 | 7/1992 | Brekke . |
| 5,152,791 | 10/1992 | Hakamatsuka et al. . |
| 5,288,496 | 2/1994 | Lewis ..................................... 424/426 |
| 5,294,446 | 3/1994 | Schlameus et al. . |
| 5,324,519 | 6/1994 | Dunn et al. ............................. 424/426 |
| 5,326,357 | 7/1994 | Kandel . |
| 5,366,508 | 11/1994 | Brekke . |
| 5,372,821 | 12/1994 | Badylak et al. .......................... 623/11 |
| 5,376,118 | 12/1994 | Kaplan et al. ............................ 623/11 |
| 5,425,639 | 6/1995 | Anders ................................... 433/169 |
| 5,478,739 | 12/1995 | Slivka et al. .............................. 623/13 |
| 5,512,475 | 4/1996 | Naughton et al. ........................ 623/11 |
| 5,520,923 | 5/1996 | Tjia et al. . |
| 5,569,463 | 10/1996 | Hezmus et al. .......................... 424/426 |
| 5,607,474 | 3/1997 | Athanasiou et al. ...................... 623/16 |
| 5,616,338 | 4/1997 | Fox, Jr. et al. .......................... 424/423 |
| 5,645,084 | 7/1997 | McKay . |
| 5,665,114 | 9/1997 | Wendock . |
| 5,736,160 | 4/1998 | Ringeisen et al. ...................... 424/487 |
| 5,830,493 | 11/1998 | Yokota et al. . |

OTHER PUBLICATIONS

Calcium Phosphate Ceramics as Hard Tissue Prosthetics, Michael Jarcho, PH.D., Clinical Orthopaedics and Related Research, No. 157, pp. 259–278 (1981).

Developmental Role of Hyaluronate, Bryan P. Toole, Connective Tissue Research, vol. 10, pp. 93–100 (1982).

Effect of fibronectin on the adhesion of an established cell line to a surface reactive biomaterial, T.L. Seitz et al., Journal of Biomedical Materials Research, vol. 16, pp. 195–207 (1982).

Influence of polylactic acid mesh on the incidence of localized osteitis, John H. Brekke et al., Oral Surg., vol. 56, No. 3, pp. 240–245 (1983).

Healing of Hyaluronic Acid–Enriched Wounds: Histological Observations, G. Abatangelo et al., Journal of Surgical Research 35, pp. 410–416 (1983).

Human Bone Morphogenetic Protein, Marshall R. Urist et al., Proceedings of the Society for Experimental Biology and Medicine 173, pp. 194–199 (1983).

Urist et al., Proc. Natl. Acad. Sci. USA, vol. 81, Jan. 1984 pp. 371–375, Purification of Bovine Bone Morphogenetic Protein by Hydroxyapatite Chromatograph.

Beta–tricalcium Phosphate Delivery System for Bone Morphogenetic Protein, Marshall R. Urist et al., Clinical Orthopaedics and Related Research, No. 187, pp. 277–280 (1984).

Effect of Surgical Trauma and Polylactate Cubes and Granules on the Incidence of Alveolar Osteitis in Madibular Third Molar Extration Wounds, John Brekke et al, J. Canad Dent Assn, No. 4, pp. 315–319 (1986).

Repair of Articular Surfaces by Allografts of Articular and Growth–Plate Cartilage, by J.E. Aston et al., The Journal of Bone and Joint Surgery, vol. 68–B, No. 1, Jan. 1986.

Spence, Basic Human Anatomy, 1986, pp. 63–65.

David H. Cormach, "Ham's Histology", Nineth Edition, ©1987, J.B. Lippincutt Company, pp. 325–326.

Sato et al., Pharm. Res., 5 (1), 21–30, 1988, Porous biodegradable microspheres for controlled drug delivery.

The Effect of the Addition of Low Molecule Weight Poly (DL–lactide) on Drug Release from Biodegradable Poly-(DL–lactide) Drug delivery Systems, R. Bodmeier et al., International Journal of Pharmaceutics, 51, pp. 1–9 (1989).

Repair of Rabbit Articular Surfaces with Allograft Chondrocytes Embedded in Collagen Gel, by S. Wakitani et al., The Journal of Bone and Joint Surgery, vol. 71–B, No. 1, Jan. 1989, pp. 74–80.

The Repair of Experimentally Produced Defects in Rabbit Articular Cartilage by Autologous Chondrocyte Transplantation, D.A. Grande et al., Journal of Orthopaedic Research, vol. 7, No. 2, 1989.

The use of polylactic acid matrix and periosteal grafts for the reconstruction of rabbit knee articular defects, H.P. von Schroeder et al., Society For Biomaterials, May 20–23, 1990.

In Vivo Osteochondrogenic Potential of Cultured Cells Derived From the Periosteum, H. Nakahara et al., Clinical Orthopaedics, Oct. 1990, vol. 259, pp. 223–232.

Cartilage resurfacing of the rabbit knee, E. Billings, Jr. et al., Acta Orthop Scand 1990; 61(3), pp. 201–206.

Potential of Adult Human Perichondrium to Form Hyalin Cartilage In Vitro, S.K. Bulstra et al., Journal of Orthopaedic Research, vol. 8, No. 3, 1990, pp. 328–335.

The use of demineralized bone and rib perichondrium composite grafts for the repair of full thickness articular defects, H.P. von Schroeder et al., 36th Annual Mtg, Orthopaedic Research Society, Feb. 5–8, 1990, New Orleans.

Reconstruction of rabbit knee articular defects with a polylactic acid matrix, R.D. Coutts et al., Orthopaedic Research Society, Feb. 5–8, 1990.

Hyaluronate can function as a cell adhesion molecule and CD44 participates in hyaluronate recogniction, by K. Miyake, C.B. Underhill, J. Lesley, and P.W. Kincade, J. Exp. Med., 172, pp. 69–75, (1990).

The use of polylactic acid matrix and periosteal grafts for the reconstruction of rabbit knee articular defects, H.P. von Schroeder et al., Journal of Biomedical Materials Research, vol. 25, pp. 329–339 (1991).

Culture–Expanded Human Periosteal–Derived Cells Exhibit Osteochondral Potential In Vivo, H. Nakahara et al., and Journal of Orthopaedic Research, vol. 9, No. 4, 1991, pp. 465–476.

Polymers, R. Langer, Bone Symposium '91, Oregon Health Sciences University, Portland, Oregon, Jul. 17–20, 1991, pp. 367–373.

The Repair of Full–Thickness Articular Cartilage Defects, N. Kawabe et al., Clinical Orthopaedics and Related Research, No. 268, Jul., 1991, pp. 279–293.

Reconstruction of rabbit knee articular defects with a polylactic acid matrix and periosteal grafts, R.D. Coutts et al., Combined Meeting/Orthopaedic Research Societies, Oct. 21–23, 1991.

Growth factor responsiveness of perichondrial cells in monolayer and attached to polylactic acid carriers, M. Lotz et al., American College of Rheumatology, Nov. 17–21, 1991.

Rib Periocondrial Autografts in Full–Thickness Articular Cartilage Defects in Rabbits, R.D. Coutts et al., Clinical Orthopaedics, Feb. 1992, vol. 275, pp. 263–273.

The Effect of a TCP–Collagen Implant on the Healing of Articular Cartilage Defects in the Rabbit Knee Joint, T. Hogervorst et al., Journal of Applied Biomaterials, vol. 3, pp. 251–258, (1992).

Bioresorbability and Biocompatibility of Aliphatic Polyesters, M. Vert et al., Journal of Materials Science: Materials in Medicine 3, ©1992 Chapman & Hall, pp. 432–446.

New Insights on the Degradation of Bioresorbable Polymeric Devices Based on Lactic and Glycolic Acids, Vert et al., Clinical Materials 10, 1992 pp. 3–8.

In vivo degradation of massive poly(a–hydroxy acids): validation of in vitro findings, M. Therin et al., Biomaterials vol. 13, No. 9, ©1992 pp. 594–600.

Scientific American, Aug. 1992, Science and Business, pp. 114–116, Material Help, Bioengineers produce versions of body tissues, by Deborah Erickson.

Rabbit articular chondrocytes in alginate gel: characterisation of immobilized preparations and potential applications, by C. Tamponnet, H. Ramdi, J–B. Guyot, and M. Lievremont, Appl. Microbiol. Biotechnol., 37, pp. 311–315, (1992).

Synthesis and turnover of proteoglycans by human and bovine adult articular chondrocytes cultured in alginate beads, by H.J. Hauselmann, M.B. Aydelotte, B.L. Schumacher, K.E. Kuettner, S.H. Gitelis, and E.J.–M.A. Thonar, Matrix, 12, pp. 116–129, (1992).

Porous polymer implants for repair of full–thickness defects of articular cartilage: an experimental study in rabbit and dog, by J. Klompmaker, H.W.B. Jansen, R.P.H. Veth, H.K.L. Nielsen, J.H. de Groot, and A.J. Pennings, Biomat., 13 (9), pp. 625–634, (1992).

Guidor, The Bioresorbable Matrix Barrier, pp. 1–33 (1993).

Compressive Characteristics of Freeze–Dried Agar and Alginate Gel, A. Nussinovitch et al., Biotechnol Prog, pp. 101–104 (1993).

Mechanisms of polymer degradation in implantable devices. 2. Poly(DL–lactic acid), S.A.M. Ali et al., Journal of Biomedical Materials Research, vol. 27, ©1993 pp. 1409–1418.

Evidence for the existence of hyaluronectin–binding proteins in the plasma membranes, Sanjay Gupta et al., FEBS 13470, vol. 336, pp. 511–515 (1993).

Towards a synthetic articular cartilage, by P.H. Corkhill, J.H. Fitton, and B.J. Tighe, J. Biomater. Sci. Polymer Edn., 4 (6), pp. 615–630, (1993).

Neocartilage formation in vitro and in vivo using cells cultured on synthetic biodegradable polymers, by L.E. Freed, J.C. Marquis, A. Nohria, J. Emmanual, A.G. Mikos, and R. Langer, J. Biomed. Mat. Res., 27, pp. 11–23, (1993).

Laminated three–dimensional biodegradable foams for use in tissue engineering, by A.G. Mikos, G. Sarakinos, S.M. Leite, J.P. Vacanti, and R. Langer, Biomat., 14 (5), pp. 323–330, (1993).

Preparation of poly(glycolic acid) bonded fiber structures for cell attachment and transplantation, by A.G. Mikos, Y. Bao, L.G. Cima, D.E. Ingber, J.P. Vacanti, and R. Langer, J. Biomed. Mat. Res., 27, pp. 183–189, (1993).

Identification of hyaluronic acid binding sites in the extracellular domain of CD44, by R.J. Peach, D. Hollenbaugh, I. Stamenkovic, and A. Aruffo, J. Cell Bio., 122 (1), pp. 257–264 (Jul. 1993).

Culture and differentiation of chondrocytes entrapped in alginate gels, by M. Grandolfo, P. D'Andrea, S. Paoletti, M. Martina, G. Silvestrini, E. Bonucci, and F. Vittur, Calcif. Tissue Int., 52, pp. 42–48, (1993).

Influence of matricial molecules on growth and differentiation of entrapped chondrocytes, by H. Rami, C. Legar, and M. Lievremont, Experi. Cell Res., 207, pp. 449–454, (1993).

Effect of freeze–dried poly–L–lactic acid discs mixed with bone morphogenetic protein on the healing of rat skull defects by T. Miki, K. Harada, Y. Imai, and S. Enomoto, J. Oral Maxillofac. Surg., 52, pp. 387–391, (1994).

Attachment and survival of perichondrocytes in a porous polylactic acid (PLA) matrix: an in vitro study, by C.R. Chu, A.Z. Monosov, R.D. Coutts, and D. Amiel, Thirteenth Southern Biomedical Engineering Conference, Apr. 16–17, 1994, University of the District of Columbia, Washington, D.C.

Expression and modulation of CD44 variant isoforms in humans, by C.R. Mackay, H–J. Terpe, R. Stauder, W.L. Marston, H. Stark and U. Günthert, J. Cell Bio., 124 (1&2), pp. 71–82, (Jan. 1994).

Controlled Release of TGF–B, From a Biodegradable Matrix for Bone Regeneration, J. Biomater, Sci. Polymer Edn., vol. 5 No. 1/2, pp. 49–63, 1993.

Structure and Function of Plasma Proteins, vol. 1, Plenum Press, London and New York, pp. 136–137.

Human Biochemistry, The C.V. Mosby Company, St. Louis, p. 440, 1982.

Polylactic Acid Surgical Dressing Material Postoperative Therapy for Dental Extraction Wounds, J Canad. Dent. Assn. No. 7, 1986, pp. 599–602.

Calvaria Repair in Monkeys Using Alloplastic–Alloimplants, The 13th Annual Meeting of the Society for Biomaterials, Jun. 2–6, 1987, New York, New York.

An evaluation of two configurations of tricalcium phosphate for treating cranioitomies, J. Biomedical Materials Research, vol. 23, No. 1, Jan. 1989, pp. 17–29.

PROCESS AND DEVICE FOR TREATING AND HEALING A TISSUE DEFICIENCY

This application is a division of U.S. application Ser. No. 08/637,651 filed Apr. 26, 1996, now U.S. Pat. No. 5,736, 160, which is a 371 of International Appln. No. PCT/US 94/12424 filed Oct. 28, 1994 and a continuation of U.S. application Ser. No. 08/144,714 filed Oct. 28, 1993, now abandoned.

BACKGROUND

1. Field of the Invention

The present invention relates to an improved method or process for treating and healing a bone void, and in particular to a method for efficiently incorporating a biologically active agent into the interstices (voids or pores) of a porous hydrophobic biodegradable material wherein the biologically active agent is deposited upon the internal surfaces defining the voids or pores of the biodegradable material.

2. Statement of Related Art

Bone wounds, as well as many other wound models, initiate a release of biologically active agents critical to the wound healing process. Bone morphogenic proteins (BMP), which naturally occur in bone, once released from the wound, stimulate osteoinduction and regenerate lost or damaged bone tissue. These same proteins, in a purified form, can be used to stimulate bone growth into a biodegradable matrix allowing for artificial creation of bone both within and external to the normal skeletal boundaries.

In recent years much work has been done in developing biodegradable porous delivery vehicles for the controlled release of substances while also providing a location for cellular attachment and guided tissue regeneration. Present biodegradable materials can be separated into two categories: 1) those which are hydrophilic; and 2) those which are hydrophobic. Hydrophilic materials (demineralized freeze dried bone, ceramic, fibrin, gelatin, etc.) possess a high affinity for water which provides for easy incorporation of the aqueous protein solutions within the internal porosity of the material, however, most are limited in their overall range of porosity, gross size, shape and mechanical characteristics. Hydrophobic materials (L-polylactic acid, D,L-polylactic acid, poly-glycolic acid, etc.), which possess little or no affinity for water, are potentially limitless in their range of porosities, gross size, shape and mechanical characteristics, but only permit easy deposition of aqueous solutions upon the external surfaces. Limited, incomplete deposition of the solution occurs within the internal porosities. This incomplete coating of the internal surfaces creates dead spaces which hinder and even prevent cellular integration. Hydrophobic materials may be impregnated with the protein creating a much more uniform distribution, but this results in a torpid release of the proteins as the polymer degrades making a large percentage of it unavailable for the critical window of time during which the protein is needed to activate regenerative processes. Thus, special procedures are required to efficiently incorporate aqueous protein solutions throughout internal porosities of hydrophobic biodegradable materials.

U.S. Patent 4,181,983 to Kulkarni and U.S. Pat. 4,186,448 to Brekke represent advances in the field of highly porous, biodegradable hydrophobic devices. Both patents show an improvement over U.S. Pat. 3,902,497 to Casey by preventing the encapsulation and isolation of the devices' interstices from a blood clot. Kulkarni and Brekke utilize a surfactant as part of the finished device in order to create a specific physical characteristic for the device; the ability to absorb fluid blood. Kulkarni and Brekke both teach that the surfactant is held in the structural filaments of the polymer and Kulkarni specifies that the surfactant must remain in the polymer in a sufficient amount to impart hydrophilicity to the device.

Stroetmann (U.S. Pat. No. 4,442,655) creates an aqueous mixture of fibrinogen (a hydrophilic material) and a biologically active substance which is then frozen and lyophilized to create a foam. This method results in the active agent being incorporated within the fibrinogen fibers and not on the surface.

Urist (U.S. Pat. No. 4,563,489) dissolved polylactic acid in a solvent forming a polymer solution. The solution was admixed with BMP and the solvent removed to create a composite which was formed into the desired shape. This method effectively traps the BMP in the polymer substance creating prolonged release kinetics which Urist states will result in bone formation over a considerable period of time. Urist (U.S. Pat. No. 4,596,574), in a separate patent, adds an aqueous solution of BMP to a hydrophilic biodegradable porous ceramic device (sintered), which is then dried to coat the internal surfaces of the device.

Caplan (U.S. Pat. No. 4,609,551) discloses a method wherein fibroblasts can be delivered to the site of a defect by immersing a biodegradable carrier in a solution of aquated BMP and fibroblasts so that the cells can attach or be trapped within the material to be implanted. All porous materials listed (fibrin clot, allograft) are hydrophilic by nature and would allow for easy integration of aqueous solutions within the matrix. Additionally, cell adhesion to a prosthesis was accomplished only on the external surface. Caplan (U.S. Pat. No. 4,620,327) further discloses a method of immobilizing BMP's on the surface of biodegradable materials using fibrin or gelatin. An aqueous solution of BMP and fibrin or gelatin is mixed and added to the biodegradable material after which it is dried trapping the BMP's.

In both Caplan patents, all porous material listed is hydrophilic, and the prosthetic devices are surface coated without mention of any internal hydrophobic porosity.

Vacanti (U.S. Pat. No. 5,041,138) discloses a method for making a cartilaginous structure utilizing a biodegradable polymer matrix. The method further comprises coating the polymer with a basement membrane (i.e. agar, gelatin, collagens, fibronectin, etc.) This coating was easily accomplished because the matrix used was an upbraided 17mm length piece of vicryl suture which formed a branching structure without an internal porosity.

SUMMARY AND DETAILED DESCRIPTION OF THE INVENTION

The present invention provides a method by which incorporation of a biologically active agent, bone morphogenic proteins (BMP), into a highly porous, biologically acceptable, biodegradable, hydrophobic polymer device, substrate, or matrix is facilitated, so hat the BMP is deposited upon the internal surfaces defining the voids or pores of the polymeric device, substrate or matrix.

The present invention, accordingly, has as an objective an improved method for:

(1) incorporating aqueous solutions or suspensions of biologically active agents within internal void chambers of a highly porous, hydrophobic biodegradable material; and (2) coating hydrophobic surfaces of void partitions with aqueous solutions or suspensions of biologically active agents.

The invention's objective is accomplished by impregnating the hydrophobic material with a surfactant before, during, or after the fabrication process which creates the materials porosity, or by coating or plating a surfactant on polymer surfaces following architecture fabrication.

Once the bone morphonogenic protein is present in the voids or pores or adhered to the internal surfaces, the device can be implanted into a bone deficiency. The BMP, which is immediately available to the wound, promotes osteoinduction by which fundamental genetic changes occur in mesenchymal cells, transforming them into osteoblasts. The polylactic acid matrix provides a biologically acceptable, calcifiable environment upon which the newly formed osteoblasts can attach. The even distribution of BMP throughout the device ensures that there will be no dead spaces within the unit. Once invested with bone, the polymer will take on water and be hydrolyzed. The end result of this hydrolysis will be energy, in the form of adenosine triphosphate (ATP), water and carbon dioxide. (Other biodegradable polymers can be used in place of the D,L-polylactic acid such as those polymers formed from hydroxy organic carboxylic acids, hydroxy aliphatic carboxylic acids, and glycollic acids.)

In its broadest aspect, the present invention provides a means for incorporation of the BMP, not only in the polymeric body and on the external surfaces of the polymeric body, but also on the internal surfaces defining the voids or pores of the body, in contrast to the prior art patents discussed above, which either have the surfactant or BMP incorporated in the polymer body composition itself, or only on the external surfaces, with limited, if any, deposition upon the internal surfaces, creating dead spaces which may hinder or even prevent cellular integration. Thus, the present invention provides for and has as an object, the impregnation of a highly porous hydrophobic material with an aqueous BMP solution so as to provide a more even distribution on the internal surfaces of the hydrophobic polymer body, resulting in a release of the proteins, independent of the polymer degradation, at the time it is needed to activate regenerative processes. Thus, unique to the present invention is the use of a surfactant to attach biologically active substances to the internal surfaces of the hydrophobic body. The present invention thus utilizes a surfactant as a manufacturing tool which allows the surfactant to be located in the polymer, on the polymer, or within the aqueous solution carrying the biologically active agent to be coated on surfaces of the implant's interstices. In view of this, once the biologically active agent is incorporated in the voids or pores of the hydrophobic body either as an aqueous solution or as a coating or on the internal surfaces of the voids, pores or interstices, it is no longer a requirement that the surfactant remain in a concentration high enough to impart hydrophilicity to the finished device.

The present invention, utilizing a surfactant as a manufacturing tool, allows the surfactant and/or any biologically active agent to be located in the polymer, on the polymer, or within the aqueous solution carrying the biologically active agent to be coated on surfaces of the implants' interstices The objectives of the present invention are accordingly reached in its broadest aspect by providing a porous hydrophobic body which is biodegradable or bioresorbable and which contains voids or pores into which an aqueous solution of surfactant and biologically active agent may be incorporated or contained as an aqueous solution, or which contains internal surfaces defining voids or pores upon which a surfactant and biologically active agent may be deposited or coated. This is accomplished by contacting the porous polymeric body with aqueous solutions of a surfactant, during or after architecture formation, and the BMP in a volume at least equal to, and preferably in a slight excess, i.e. up to about 10%, of the volume of the voids or pores of the polymeric device, body or substrate, and drying, either with a desiccator or by air drying at ambient temperatures or at elevated temperatures up to about 40° C. This procedure results in efficient incorporation of the aquated proteins throughout the internal porosities of the hydrophobic biodegradable materials either as an aqueous solution or as a coating on the internal surfaces defining the voids or pores.

The method for preparing the porous hydrophobic body preferably comprises dissolving the polymer in a solvent such as acetone, chloroform, ethanol or t-butanol and filtering. The surfactant and/or any biologically active agent, if it is to be incorporated into the polymer itself, is added to and admixed with the polymer solution. The material is then treated to remove residual solvent. Precipitating the polymer, lyophilizing the solution, evaporative distillation or other method is used to remove the solvent. If not already of a porous form, the polymer can be shaped by several different methods in order to create an internal porosity (i.e. ground and sintered, drawn into threads and woven into layered sheets, extruded followed by formation of pores or voids therein or spun to form a cotton candy type mass, etc.) An AccuPyc 1330 helium pychometer is used to determine the exact polymer volume of each unit. This value is subtracted from the apparent volume, yielding void volume of each device.

Addition of the surfactant, if not already done during the forming process, may be accomplished in three steps.

(1) Dissolve a mass of triethanolamine dodecylbenzene sulfonate, equal to 5% of the mass of the polymer delivery device, in an aqueous solution of a volume that with the addition of the volume of surfactant will be equal to that of the void volume of the implant. Matching the surfactant solution volume with the device void volume ensures that all internal surfaces come into contact with the solution. BMP can be added to the solution at this time if desired.

(2) Inject and/or press the surfactant solution into the device so that the entire volume of solution is held within the polymer unit. The surfactant breaks the surface tension of the aqueous solution allowing it to flow into the device.

(3) Place device into a desiccator and remove the water leaving the surfactant coating the internal surfaces of the voids.

Addition of the BMP, if not added with the triethanolamine dodecylbenzene sulfonate, is accomplished in the same manner as the addition of the surfactant.

(1) The desired quantity of BMP is admixed to a volume of aqueous solution so that the new solution volume is equal to that of the void volume of the delivery vehicle.

(2) Inject and/or press the protein solution into the device so that the entire volume of solution is held within the polymer unit. (The surfactant breaks the surface tension of the aqueous solution allowing it to flow into the device.

(3) Place device into a desiccator and remove the water leaving the protein coating the internal surfaces of the voids.

The process may be practiced by impregnating first with the surfactant in the required volume followed by impregnation with a solution of the BMP, again in the required volume, preferably with drying after the first impregnation with the surfactant. In an alternate method, the surfactant may be introduced along with the BMP in the required volume to impregnate the polymeric body followed by drying.

The body, containing the surfactant and biologically active agent within its pores or having its surfaces, particularly substantially all the internal void surfaces, coated with protein cargo uniformly deposited on its polymer surfaces, is then used in treating bone defficiencies as described in the prior art patents discussed above. The device or body is implanted into the bone deficiency area, the body having been fashioned or shaped to the size and shape of the bone deficiency cavity. Once implanted, the device provides a biologically acceptable environment for cell migration and attachment while delivering its biologically active agents to the wound site, stimulating cell chemotaxis and osteoinduction. Over a period of time, the polymer body degrades, the rate of degradation varying dependent on its overall mass, molecular weight, and the polymer surface area, external and internal exposed to interstitial fluid.

Another aspect of the present invention is the provision of an implant device or body of a biodegradable or bioresorbable material which provides lessened inflammatory reactions. Biodegradation of massive poly(alpha-hydroxy) acids proceeds heterogeneously and proceeds faster in the center than at the surfaces of the specimens. This phenomenon, in amorphous polymers (D, L-polylactic acid), is due to autocatalysis inside of the polymer body initiated by free carboxyl groups which are unable to diffuse out of the material to be carried away by the interstitial fluid. This results in a bimodal molecular weight distribution similar to that caused by the presence of crystalline areas in other members of the poly(alpha-hydroxy) acid family, and in other biodegradable polymers. The central part of the polymer body becomes a viscous liquid and eventually is released into the surrounding tissues. This flood of oligomers may create an inflammatory reaction which irritates the already traumatized tissues and may result in additional complications It was now discovered that the undesirable inflammatory reaction does not occur, or is minimized if each point within the polymer mass of the hydrophobic body is within 0.5 mm from an external surface which is in contact with interstitial fluid. It is accordingly an object of this invention to provide a device for treating bone deficiencies comprised of a hydrophobic polymeric body which is biodegradable or bioresorbable in which no point within the polymer mass or body is greater than about 0.75 mm from an external surface which is in contact with interstitial fluid, thereby allowing for slow diffusion of oligomers from the polymeric hydrophobic body or device and preventing or minimizing a sudden flooding of the tissues by the oligomers. While this aspect of the invention is applicable to the hydrophobic bodies of the present invention having internal surfaces defining voids or pores, it is also applicable to bodies formed of solid sheets less than 1.5 mm in thickness, surgical sutures, polymer microspheres and the like.

The preferred hydrophobic material, forming the body or device for treating a bone deficiency or cavity, is D,L-polylactic acid. Other hydrophobic materials are, however, also suitable, such as L-polylactic acid and polyglycolic acid and polymers of other alpha-hydroxy carboxylic acids, poly (alpha-hydroxy) acids. In general, any hydrophobic material which is biodegradable or bioresorbable and capable of polymerization to a polymeric form or otherwise formed to a body having pores or voids, may be employed in the present invention. The polymerizable material, such as the preferred D,L-polylactic acid, is processed, i.e. foamed or woven into layered sheets and formed to the size or shape of the bone deficient cavity. Once the material is formed into the desired shape and size, it is then dipped or otherwise contacted with the aqueous solution of surfactant and the osteoinductive protein, in a volume, preferably in a slight excess over the void volume of the device. The device now containing the osteoinductive protein incorporated on substantially all its external and internal void or pore surfaces, is then dried. Drying may be accomplished by simple air drying, preferably in a desiccator, removing the water and leaving a coating or deposit of the osteoinductive protein on the surfaces. In general, the process thus comprises:

(a) providing a porous hydrophobic biodegradable or bioresorbable body;

(b) contacting the hydrophobic body with an aqueous solution of a physiologically acceptable surfactant and a biologically active agent, preferably an osteoinductive, protein; and (c) drying the hydrophobic body so as to leave the osteoinductive protein, biologically active agent deposited on the external and internal surfaces of the hydrophobic body.

In step (b) above, the hydrophobic body is impregnated with the surfactant and biologically active agent in an aqueous solution of a volume in an excess of the void volume of the hydrophobic body, up to an excess of 10% of the void volume.

Further in step (b), the surfactant may be admixed with the biologically active agent prior to contacting the hydrophobic body or alternatively, an aqueous solution of the surfactant may be used alone to impregnate the hydrophobic body, followed by drying after which the body is then contacted by an aqueous solution of the biologically active agent prior to final drying.

In the method, the biologically active agent, primarily of interest, is an osteoinductive agent and/or agents stimulating cell chemotaxis. Other biologically active agents which may be employed are physiologically acceptable drugs, biological modifiers, proteins, hormones, antigens, alone or mixtures thereof.

The surfactants which may be employed are any physiologically acceptable, i.e. non-toxic anionic, cationic, amphoteric or nonionic surfactant compatible with the biologically active agent and the hydrophobic body. The surfactant may be present in the aqueous solution in a concentration effective to provide up to about a 10% increase in the mass of the polymer. The preferred surfactant is triethanolamine dodecyl benzene sulfonate; however, as a class, the alkali metal soaps of fatty acids or the alkyl, aryl sulfonic acids are also suitable. Thus, the surfactants may include: linear aklylbenzene sulfonates, alky sulfates, alcohol ethoxylates, alcohol ethoxy sulfates, alkylphenol ethoxylates, alpha olefin sulfonates, secondary alkane sulfonates, and alpha olefin sulfonates.

The foregoing process provides for an improvement over prior art processes to provide efficient incorporation of biologically active agents, particularly osteoinductive agents into hydrophobic bodies used to fill bone deficiencies (cavities). The use of a surfactant to attach the biologically active agents to the internal surfaces of the device provides for the improved performance. The invention permits the surfactant and biologically active agent to be coated on the internal void surfaces or implant interstices, or on the external surfaces of the hydrophobic polymer body, and if desired the surfactant and biologically active agents may still be incorporated into the polymeric body structure itself during fabrication, thus providing increased effectiveness over the prior art earlier described. For example, Brekke U.S. Pat. No. 4,186,448 specifically teaches against voids holding a therapeutic material indicating the agents should be held in the structural filaments of the polymer itself. Brekke U.S. Pat. No. 5,133,755 discloses in the preferred form injection by the operating surgeon or an assistant of an aqueous solution of the biologically active agent into the macro-structure device just prior to introduction of the device into the bone deficiency void or cavity, having the disadvantage of handling aqueous solutions at that time. While the present invention does not intend to exclude the introduction of an aqueous solution of the biologically active agent into the internal voids or pores, without drying, prior to introduction into the bone deficiency cavity, the preferred embodiment of the present invention resides in drying so as to remove the water, leaving a deposit of the surfactant and the biologically active agent on the internal surfaces defining the voids or pores of the polymeric hydrophobic body. While Kulkarni and Brekke utilize a surfactant in the hydrophobic body, Kulkarni specifies the surfactant must remain in the polymer in an amount sufficient to impart hydrophilicity to the device. In contrast, the present invention, while not excluding the presence of surfactant in the formation of the polymer structure itself, provides for attachment of the biologically active agents on the external and internal void surfaces or interstices, no longer requiring the surfactant to remain in a concentration high enough to impart hydrophilicity to the finished body or device. In many instances, it is beneficial to have a porous, surface coated, hydrophobic, delivery device.

While the Kulkarni and Brekke patents utilize a surfactant as part of the polymeric body itself, neither recognizes any potential use of the internal surfaces defining the voids or pores as a biologic carrier and, as noted above, Brekke specifically teaches against the voids holding a therapeutic material indicating the agents should be held in the structural filaments of the polymer. In the first Urist Patent (U.S. Pat. No. 4,563,489), the BMP is also effectively trapped in the polymer substance itself creating prolonged release kinetics over a considerable period of time. In contrast, the present invention coats the internal surfaces of the hydrophobic body which allows for immediate release of the biologically active substance. In the second Urist Patent (U.S. Pat. No. 4,596,574), the BMP solution is added to a hydrophilic, not a hydrophobic, device.

Having thus described the invention, what is claimed as new and desired to be secured by Letters Patent is:

1. An improved process for treating and healing a tissue deficiency by incorporating biologically active agents onto the internal surfaces of a porous hydrophobic biodegradable or bioresorbable body, comprising:
    (a) providing a hydrophobic biodegradable or bioresorbable body formed of a polymerized alpha hydroxy acid and having external surfaces, and voids or pores within the hydrophobic body presenting internal surfaces, with voids or pores providing a biologically acceptable environment cell migration and attachment onto the internal surfaces of the hydrophobic body, in which the hydrophobic body is capable of being shaped to conform to the size and shape of the tissue deficiency to be treated and healed;
    (b) contacting the hydrophobic body with an aqueous solution of a physiologically acceptable surfactant and a biologically active agent whereby the surfactant and the biologically active agent are deposited on the internal surfaces of the voids or pores of the hydrophobic body; and
    (c) applying the hydrophobic body containing the biologically active agent into the tissue deficiency to be treated and healed.

2. A method as defined in claim 1 wherein the aqueous solution of surfactant and biologically active agent is contained within the voids or pores of the hydrophobic body.

3. A method as defined in claim 1 wherein the hydrophobic body contacted by the aqueous solution is dried after step (b) whereby said biologically active agent is deposited on the internal surfaces defining the voids or pores of the hydrophobic body, prior to application of the hydrophobic body into the tissue deficiency in step (c).

4. A method as defined in claim 3 wherein the hydrophobic body contains the surfactant or biologically active agent in the body structure itself, as well as on the external surfaces therof and on the internal surfaces defining the voids or pores of the hydrophobic body.

5. A method as defined in claim 1 wherein the hydrophobic body has no point within the body greater than 0.75 mm from a surface which will be in contact with interstitial fluid upon implantation.

6. A method of incorporating biological agents comprising:
    (a) providing a porous hydrophobic biodegradable or bioresorbable substrate including internal surfaces defining voids or pores providing a biologically acceptable environment for cell migration and attachment onto the internal surfaces of the substrate,
    (b) contacting the hydrophobic substrate with an aqueous solution of a physiologically acceptable surfactant and a biologically active agent in a volume at least matching and up to about a 10% excess of the volume of the pores or voids of the hydrophobic substrate whereby the pores or voids of the hydrophobic substrate are filled with the aqueous solution, with the physiolocally acceptable sufactant being at least one of a group consisting of: alkali metal soaps of fatty acids, alkyl sulfonic acids, linear aklylbenzene sulfonates, alky sulfates, alcohol ethoxylates, alcohol ethoxy sulfates, alkylphenol ethoxylates, alpha olefin sulfonates, secondary alkane sulfonates, and alpha olefin sulfonates; and
    (c) drying the hydrophobic substrate whereby the water is removed leaving a coating of the biologically active agent on the internal surfaces defining the voids or pores in the hydrophobic substrate.

7. A method as defined in claim 6 wherein the hydrophobic substrate is contacted with an aqueous solution containing both the surfactant and the biologically active agent.

8. A method as defined in claim 6 wherein the hydrophobic substrate is first contacted with an aqueous solution of a surfactant and dried prior to contacting the hydrophobic substrate with an aqueous solution of the biologically active agent.

9. A method as defined in claim 6 wherein said surfactant is a physiologically acceptable anionic, cationic, amphoteric or nonionic surfactant.

10. A method as defined in claim 6 wherein the surfactant is triethanol amine dodecyl benzene sulfonate.

11. A method as defined in claim 6 wherein said biologically active agent is selected from the group consisting of a physiologically acceptable drug, a biological modifier, a protein, a hormone, an antigen, and mixtures thereof.

12. A method as defined in claim 11 wherein the biologically active agent stimulates tissue induction.

13. A method as defined in claim 11 wherein the biologically active agent stimulates cell chemotoxis.

14. A method as defined in claim 6 wherein said drying comprises exposing the hydrophobic body containing the surfactant and biologically active agent to a desiccator.

15. A method as defined in claim 6 wherein the drying is conducted by air drying at ambient or elevated temperatures.

16. A method as defined in claim 6 wherein the hydrophobic substrate comprises a polymerized alpha-hydroxy acid.

17. A method as defined in claim 16 wherein the polymerized alpha-hydroxy acid is D,L-polylactic acid.

18. A method of coating biologically active agents comprising:
   (1) providing a porous hydrophobic biodegradable or bioresorbable material, with the hydrophobic material including internal surfaces defining voids or pores providing a biologically acceptable environment for cell migration and attachment onto the internal surfaces of the hydrophobic material;

(2) contacting the porous hydrophobic material with an aqueous solution of a physiologically acceptable surfactant with a volume at least matching and up to about a 10% excess over the volume of the pores or voids in the hydrophobic material, with the physiologically acceptable surfactant being at least one of a group consisting of: alkali metal soaps of fatty acids, alkyl, aryl sulfonic acids, linear alkylbenzene sulfonates, alky sulfates, alcohol ethoxylates, alcohol ethoxy sulfates, alkylphenol ethoxylates, alpha olefin sulfonates, secondary alkane sulfonates, and alpha olefin sulphonates;

(3) removing the water from the aqueous solution by desiccation, whereby the surfactant is deposited on the internal surfaces defining the pores or voids in the hydrophobic material;

(4) contacting the porous hydrophobic material containing the surfactant on the internal surfaces with an aqueous solution or a biologically active agent; and (5) removing the water from the aqueous solution of the biologically active agent whereby the biologically active agent is deposited onto the internal surfaces defining the pores or voids in the hydrophobic material.

19. A porous biodegradable or bioresorbable hydrophobic body structure or device comprising a hydrophobic polymer of an alpha hydroxy ac an having pores or voids therein and (a) internal surfaces defining the voids or pores which provide a biologically acceptable environment for cell migration and attachment onto the internal surfaces of the hydrophobic polymer and (b) external surfaces and containing a physiologically acceptable surfactant in the body structure itself and a biologically active agent in the pores or voids either (x) as an aqueous solution or (y) coated on the internal surfaces defining the voids or pores, as well as on the external surfaces of the body structure.

20. A porous biodegradable or bioresorbable hydrophobic body structure or device as defined in claim 19 wherein said surfactant is also contained in the voids or pores either as an aqueous solution or coated an the internal surfaces defining the voids or pores, as well as coated on the external surfaces.

21. A porous bioresorbable hydrophobic body structure or device as defined in claim 20, wherein the aqueous solution in the voids or pores contains both the surfactant and the biologically active agent.

22. A porous biodegradable or bioresorbable hydrophobic body structure or device as defined in claim 19 wherein the polymer is a polymer or an alpha-hydroxy carboxylic acid.

23. A porous biodegradable or bioresorbable hydrophobic body structure or deice as defined in claim 19 wherein the polymer is polymerized D,L-polylactic acid.

24. A biodegradable or bioresorbable hydrophobic polymeric body adapted for implantation into a body cavity, which polymeric body on assimilation breaks down into its oligomers, comprising, in combination: a porous polymeric material composed of a polymer of an alpha hydroxy acid and including internal surfaces defining voids or pores providing a biologically acceptable environment for cell migration and attachment onto the internal surfaces of the porous polymeric material and in which no point within the porous polymeric material is greater than about 0.75 mm from a surface which will be in contact with interstitial fluid upon implantation; and a biologically active agent incorporated into the porous polymeric material.

25. A polymeric body as defined in claim 24 wherein the body comprises a polymer of an alpha-hydroxy carboxylic acid.

26. A polymeric body as defined in claim 24 wherein the polymeric body comprises polymerized D,L-polylactic acid.

* * * * *

UNITED STATES PATENT AND TRADEMARK OFFICE
CERTIFICATE OF CORRECTION

PATENT NO : 5,935,594

DATED : August 10, 1999

INVENTOR(S) : Ringeisen, et al.

It is certified that error appears in the above-identified patent and that said Letters Patent is hereby corrected as shown below:

Page 2, right column, Line 35, cancel "recogniction" and substitute therefor --recognition.--.

Col. 2, Line 2, after "blood." start a new paragraph.

Col. 2, Line 56, cancel "hat" and substitute therefor --that--.

Col. 3, Line 57, after "interstices" insert --.--.

Col. 8, Line 38, add "aryl" before "sulfonic acids".

Col. 10, Line 13, cancel "an" and substitute therefor --on--.

Col. 10, Line 23, cancel "deice" and substitute therefor --device--.

Signed and Sealed this

Seventh Day of March, 2000

Attest:

Attesting Officer

Q. TODD DICKINSON

Commissioner of Patents and Trademarks